US00PP20460P2

(12) United States Plant Patent
Kwantes

(10) Patent No.: US PP20,460 P2
(45) Date of Patent: Nov. 10, 2009

(54) *BRUNNERA* PLANT NAMED 'EMERALD MIST'

(50) Latin Name: *Brunnera macrophylla*
Varietal Denomination: Emerald Mist

(75) Inventor: Michael G. Kwantes, Allegan, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 12/229,276

(22) Filed: Aug. 21, 2008

(51) Int. Cl.
*A01H 5/00* (2006.01)

(52) U.S. Cl. ..... Plt./412

(58) Field of Classification Search ..... Plt./263, Plt./412
See application file for complete search history.

*Primary Examiner*—Susan B McCormick Ewoldt

(57) ABSTRACT

The new the new and distinct perennial *Brunnera macrophylla* plant named 'Emerald Mist' possesses a patterned dense silver baring on the outer portion of the foliage, a green center portion and a light silver dusting over the entire green leaf portion between the veins. It is accented by light blue flowers in spring and is useful for landscaping, potted plants display or cut flower or foliage use.

2 Drawing Sheets

Botanical classification: *Brunnera macrophylla* (J.F. Adams) I.M. Johnst. Variety denomination: 'Emerald Mist'.

SUMMARY, BACKGROUND AND ORIGIN OF THE PLANT

The new and distinct *Brunnera macrophylla* 'Emerald Mist', hereinafter also referred to as 'Emerald Mist' and the "new plant," is a new and distinct mutation of the cultivar *Brunnera macrophylla* 'Jack Frost' US PP13859. The new plant was discovered by Michael G. Kwantes as a non-induced whole plant mutation among some propagated B. 'Jack Frost' in cultivation in the greenhouse of a nursery in Zeeland, Mich. The new plant has been asexually propagated, both by crown division, and by careful tissue culture propagation of shoot tips, at the same nursery in Zeeland, Mich. Both asexual propagation methods have produced plants identical to the originally discovered plant and maintain those unique characteristics in subsequent generations.

'Emerald Mist' is different from all other *Brunnera* known to the inventor. The most similar plants are 'Jack Frost' (US PP13859), 'Looking Glass' (US PP17829), 'Silver Wings' (US PP13706) and 'Langtrees' (not patented). 'Jack Frost' and 'Looking Glass' have a much denser silver portion on the leaf. 'Silver Wings' has the denser silver portion similar to 'Jack Frost' but with a thin margin of a lighter white. The new plant has a silver pattern that is more broken than any of these, but larger and with more numerous spots than 'Langtrees'.

'Emerald Mist' also develops a very light dusting of silver over the entire leaf giving it a type of two-tone silvering. 'Jack Frost' and 'Looking Glass' and 'Silver Wings' have only the one color silver, and 'Langtrees' does not have this lighter dusting.

BRIEF DESCRIPTION OF THE DRAWINGS

The photographs of the new invention demonstrate the overall appearance of the plant including the unique traits. The colors are as accurate as reasonably possible with color reproductions. Light source direction may cause the appearance of variation in color.

DETAILED BOTANICAL DESCRIPTION OF THE PLANT

Figure 1:
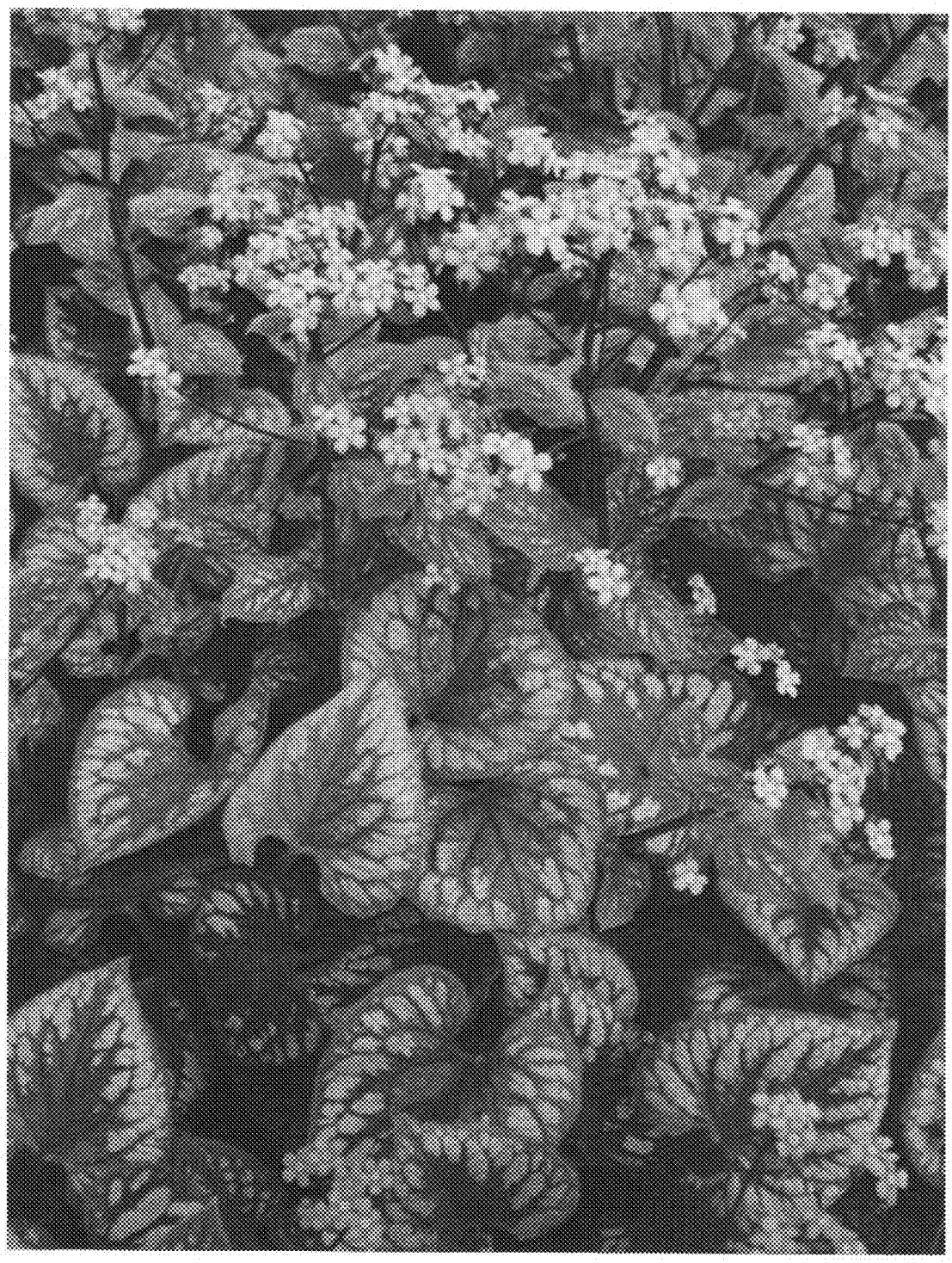
FIG. 1 shows the overall plant while flowering in mid spring.
Figure 2:
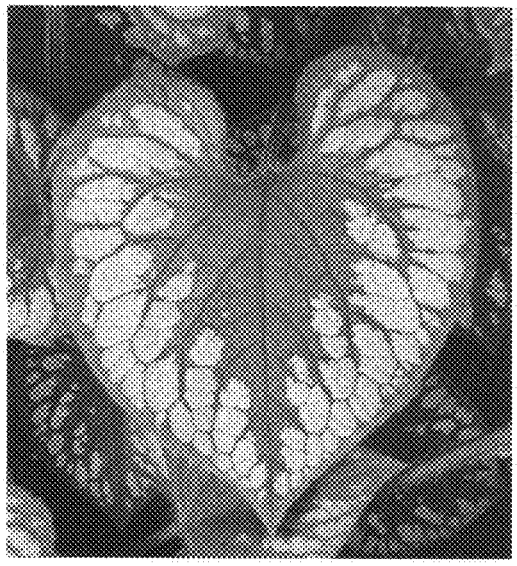
FIG. 2 shows a close-up of foliage with the unique variegation in mid summer.
Figure 3:
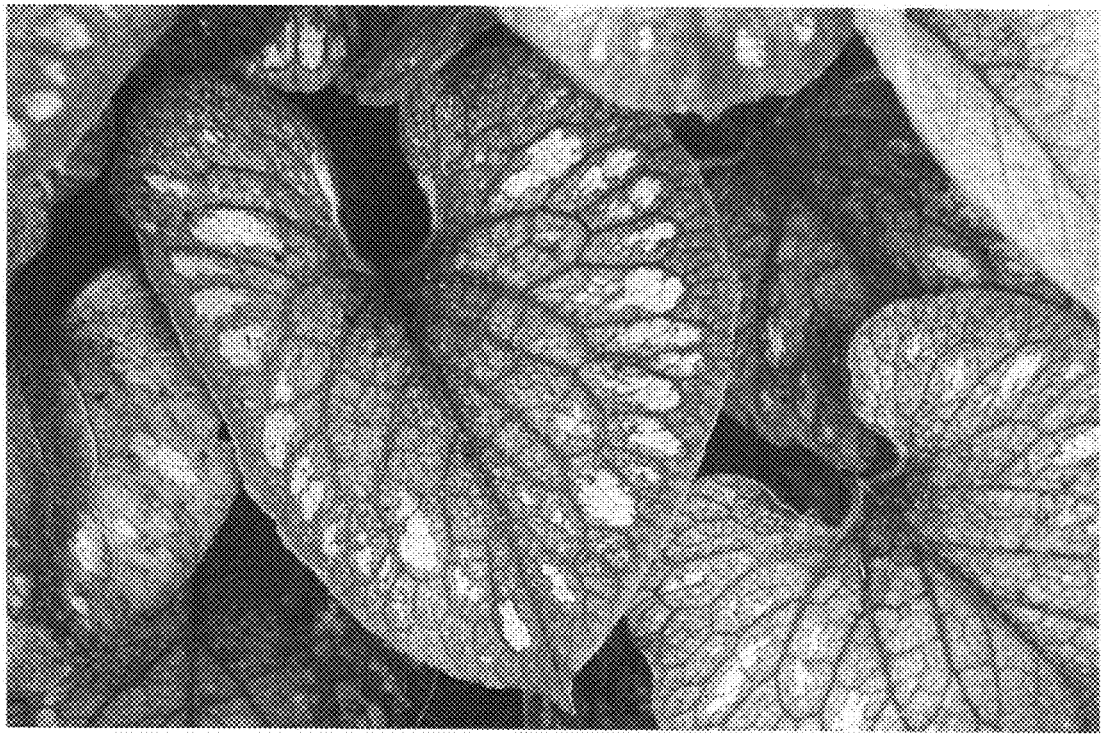
FIG. 3 shows a close-up of the foliage later in the season wit less barring.

The following descriptions with generic dictionary color usage are of a three-year-old plant growing in Zeeland, Mich. For more precise color descriptions The Royal Horticultural Colour Chart and the corresponding color references are used. The plant has not been evaluated in all possible growing environments. The phenotype may vary slightly with different conditions such as fertility, light, moisture and temperature, however the genotype remains stable.

Plant habit: mounded, clumping spring-flowering perennial about 40 cm tall and 40 cm wide; leaves cordate to reniform, coarsely pubescent with long thin petioles basally attached to underground rhizomes;

Root: fibrous, branched.

Growth rate: vigorous.

Foliage description:

*Lamina.*—Primarily cordate to deltoid, broadly acute apex with cordate base, entire; pubescent (hirtellous) top and bottom surfaces about 15 cm wide and 15 cm long;

*Color spring.*—underside RHS 138B with main veins RHS 138D and minor veins RHS 138B; top surface closest to RHS 137B on edge of leaf with irregular shaped and sized blotched patterns closest to RHS 191C broken between veins and frequently filling in between the veins in all but the margin 1 cm and center one third of the leaf, the larger patches about 3 cm long and 1 cm wide with some smaller patches about 2 mm in diameter as well as other sizes between;

center one third of lamina normally devoid of silver patches; main veins of RHS 138A and minor veins not noticeable;

*Color summer.*—underside closest to RHS 191A with main veins RHS 138D and minor veins RHS 137A; top surface closest to RHS 137A on edge of leaf with irregular shaped and sized blotched patterns between veins usually in radial formation closest to RHS 191C broken between veins, the larger patches about 3 cm long and 1 cm wide with some smaller patches about 2 mm in diameter as well as other sizes between; Center one third of lamina normally devoid of silver patches; developing a light silver dusting between the veins producing a color more green than RHS 189C and more gray than RHS N138C, and main veins of RHS 139A and minor veins not noticeable;

*Veins.*—Palmate, main center vein 2 mm to 3 mm diameter;

*Petiole.*—Hirtellous, rounded on adaxial side, concave on abaxial side; about 22 cm long and 3 at top and 4 mm wide at base; RHS 146D at base and RHS 146C with slight reddish purple tint in areas exposed to more light;

*Flower description.*—Numerous flowers, about 150, on paniculate cymes with small ovate cauline leaves either sessile or with short petioles; individually about 8 mm across; inflorescence up to 45 cm tall and branches to 15 cm wide; effective for three weeks beginning late April in most years; individual flower effective up to a week; self-cleaning;

*Petals.*—Five, entire, glabrous, rounded apex, individually about 3 mm across, basally fused to form corolla tube about 7 mm in diameter; face is between RHS 106A and RHS 107B with a center eye lighter than RHS 108D; back of petals about RHS 108D;

*Sepals.*—Five, about 1.5 mm across and between 1.5 and 2.0 mm long; RHS 144B;

*Buds.*—Globose, about 2 mm in diameter, RHS 76C about two days prior to opening;

*Peduncles.*—Pubescent to hirtellous, erect to 60 cm tall and 4 mm in diameter; between RHS N77A and RHS N77B;

*Pedicels.*—Pubescent to hirtellous, about 3 mm long and 1 mm wide; RHS 138B;

*Gynoecium.*—Single, 3 mm long, about RHS 193 D.

*Androecium.*—Five; stamens white, about 2.5 mm long; anthers 1 mm long and RHS N 187A.

*Pollen.*—Less than 0.2 mm, nearest RHS 155D;

*Seed.*—Are identical to the species; a small nutlet, less than 1 mm in diameter, dark brown to near black nearest RHS 200A;

The plant is hardy to USDA zone 3. It is susceptible to slugs, but has no serious pests that are uncommon to *Brunnera*. The new plant performs well in shade, or partly sunny garden locations with some protection from the hottest sun. It grows best with an ample amount of moisture, but can tolerate drier gardens once established. It is well-suited for landscaping in containers, and is less prone to leaf scorch than either *Brunnera* 'Variegata' or 'Silver Wings'.

Claim:

1. I claim the new and distinct perennial *Brunnera macrophylla* plant named 'Emerald Mist' as herein described and illustrated, having a dense silver baring on the outer portion of the foliage, a green center portion and a developing a light silver dusting over the entire green leaf portion, accented by light blue flowers in spring and useful for landscaping, potted plants display or cut flower or foliage use.

* * * * *